(12) United States Patent
Ikhlef et al.

(10) Patent No.: US 11,504,085 B2
(45) Date of Patent: Nov. 22, 2022

(54) METHOD FOR CALIBRATING DEFECTIVE CHANNELS OF A CT DEVICE

(71) Applicant: MinFound Medical System CO., Ltd., Shaoxing (CN)

(72) Inventors: Aziz Ikhlef, Shaoxing (CN); Zheng Chu, Shaoxing (CN); Yaofa Wang, Shaoxing (CN)

(73) Assignee: MINFOUND MEDICAL SYSTEM CO., LTD., Shaoxing (CN)

( * ) Notice: Subject to any disclaimer, the term of this patent is extended or adjusted under 35 U.S.C. 154(b) by 702 days.

(21) Appl. No.: 16/520,354

(22) Filed: Jul. 24, 2019

(65) Prior Publication Data

US 2020/0390414 A1 Dec. 17, 2020

(30) Foreign Application Priority Data

Jun. 13, 2019 (CN) .......................... 201910509859.8

(51) Int. Cl.
*A61B 6/00* (2006.01)
*G01T 7/00* (2006.01)
*G06N 3/08* (2006.01)
*G06T 5/00* (2006.01)
*G06T 11/00* (2006.01)

(52) U.S. Cl.
CPC .............. *A61B 6/585* (2013.01); *A61B 6/42* (2013.01); *G01T 7/005* (2013.01); *G06N 3/08* (2013.01); *G06T 5/001* (2013.01); *G06T 11/005* (2013.01); *G06T 2207/10081* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

2006/0262895 A1* 11/2006 Kawachi ............. G01N 23/046
378/4
2018/0374245 A1* 12/2018 Xu ......................... G06T 11/005
2019/0206096 A1* 7/2019 Fu ......................... G06T 7/0012
2020/0305806 A1* 10/2020 Tang .................... A61B 6/5205

* cited by examiner

Primary Examiner — Leon Viet Q Nguyen
(74) Attorney, Agent, or Firm — Leong C. Lei

(57) ABSTRACT

A method for calibrating defective channels of a CT device involves in a step S10, acquiring original data collected by the CT device; in a step S20, capturing to-be-recovered areas from the original data, wherein the to-be-recovered areas contain the defective channels of the CT device; in a step S30, inputting data of the to-be-recovered areas to a neural network for training so as to generate training results; and in a step S40, using the training results to repair the to-be-recovered areas. The method eliminates effects of artifacts caused by defective channels on image reconstruction.

8 Claims, 5 Drawing Sheets

METHOD FOR CALIBRATING DEFECTIVE CHANNELS OF A CT DEVICE

BACKGROUND OF THE INVENTION

1. Technical Field

The present invention relates to medical technologies, and more particularly to a method for calibrating defective channels of a CT device.

2. Description of Related Art

Computed tomography (CT) is a technology that uses precise, calibrated X rays, γ rays, and ultrasonic waves in conjunction with high-sensitivity detectors to perform scanning and produces section scans one by one around a certain part of a human body. With the ability to figure out the shape, structure and possible material of a scanned object using transmittance of rays (X rays, γ rays, and ultrasonic waves) at different angles, CT has the benefits about fast scanning and clear images, and is useful in detection of a wide range of diseases. A typical multi-detector CT device has channels (detectors) in an amount ranging from tens of thousands to hundreds of thousands. These channels tend to have uneven performance, which means some rays unable to properly respond to incidence become defective channels that lead to ring artifacts during image reconstruction, in turn degrading clinical diagnosis.

In order to ensure the quality of clinical diagnosis, it is necessary to eliminate the effects of defective channels on image reconstruction without causing additional artifacts. To do this, the actual attenuation of rays at the sits of defective channels has to be calculated. This is traditionally achieved by acquiring measured values of usable channels around a failed channel and estimating the actual attenuation of rays at the defective channel by means of interpolation or averaging calculation. However, the known approach has its shortcomings.

The first issue to be addressed is about inaccurate estimation of high-frequency information, which leading to streak artifacts with respect to some certain angles. The second issue is that significant errors tend to happen in case of continuous damaged detectors, which brings about ring artifacts that are relatively pale.

Hence, how to provide a method for calibrating defective channels of a CT device that eliminates effects of artifacts caused by defective channels on image reconstruction has become a pressing issue to be addressed in order to ensure the quality of clinical diagnosis.

SUMMARY OF THE INVENTION

An objective of the present invention is to provide a method for calibrating defective channels of a CT device that eliminates effects of artifacts caused by defective channels, and particularly defective channel clusters with a large area, on image reconstruction, thereby ensuring the quality of clinical diagnosis.

The present invention is realized through a method for calibrating defective channels of a CT device, which comprises the following steps:

the step S10, acquiring original data collected by the CT device;

the step S20, capturing to-be-recovered areas from the original data, wherein the to-be-recovered areas contain the defective channels of the CT device;

the step S30, inputting data of the to-be-recovered areas into a neural network for training so as to produce training results; and the step S40, using the training results to repair the to-be-recovered areas.

Further, the step S10 particularly is: acquiring the original data collected by the CT device as three-dimensional data A0(Channels, Rows, Views), where Channel s represents channel directions of detectors of the CT device, ROWs represents row directions of the detectors, and Views represents rotation angle directions of the detectors, with each said rotation angle direction covering N defective channels.

Further, the step S20 particularly involves:

in the step S21, reading coordinates of the defective channels in the form of index=(Channels, Rows);

in the step S22, defining the to-be-recovered area Map sized Wd*Wd against the coordinates of the defective channels as respective centers, with dimensions of the entire to-be-recovered areas being Wd*Wd*N*Views, where Wd is an integer and Wd≥1;

in the step S23, normalizing the to-be-recovered areas Map; and in the step S24, marking areas where training in the neural network has to be performed in normalized data.

Further, the step S23 particularly is:

defining an operator Norm(N, Views)=maximum(Map (:, :, N, Views)), representing finding a maximum of each said to-be-recovered area Map sized Wd*Wd; and normalizing the to-be-recovered areas Map to [0,1]: MapNorm=Map/Norm or normalizing the to-be-recovered areas Map to [$\Delta1$, 1]: MapNorm=Map/Norm*2−1, where MapNorm represents the normalized data.

Further, the step S24 particularly is:

marking the area to receive neural network training as MapMask, and $$MapMask = \begin{cases} C & \left|i - \frac{W_d}{2}, j - \frac{W_d}{2}\right| < h \\ MapNorm & \text{else} \end{cases};$$

where C represents an arbitrarily marked mask value; h represents a width of mask; the operator ∥ represents calculating the 2nd norm; i represents a number of the channel directions of the detectors, and i>0; j represents a number of the row directions of the detectors, and j>0.

Further, the step S30 particularly involves:

in the step S31, building the neural network as an adversarial neural network using a first neural network and a second neural network; and in the step S32, inputting MapNorm and MapMask to the adversarial neural network for training, and producing the training results MapAI each having the same size as MapNorm.

Further, the step S40 particularly involves:

in the step S41, performing strength recovery on the training results MapAI;

in the step S42, calculating data offsets offset of the training results MapAI; and in the step S43, recovering the to-be-recovered areas according to the training results MapAI after strength recovery, the data offsets offset and the original data A0.

Further, the step S41 particularly is:

defining data of each said rotation angle direction after strength recovery MapRec (:, :, N, Views)=(MapAI (:, :, N, Views)+1)*Norm(N, Views)/2.

Further, the step S42 particularly is:
defining a matrix template sized Wd*Wd, $$Ref\ Mask = \begin{cases} 1 & L1 < \left| i - \frac{W_d}{2}, j - \frac{W_d}{2} \right| < L2 \\ 0 & else \end{cases},$$

and L2−L1>h; and defining the data offsets offset=(A0−MapRec)*RefMask/sum(Ref Mask), where sum(Ref Mask) represents a sum of all elements in Ref Mask.

Further, the step S43 particularly involves:

in the step S431, reproducing the original data A0 as data A1;

in the step S432, resetting the coordinates of the defective channels to Corr Val, and Corr Val=offset (N, Views)+Map Rec (i, j, N, Views) according to data offset offset and original coordinates index=(Channels, Rows) of the defective channels; and in the step S433, updating the training results MapAI after strength recovery to the data A1 according to the reset coordinates Corr Val.

The present invention advantageously employs a neural network to perform training on data in areas to be recovered and thereby supplementing texture of the to-be-recovered area but not simply performing interpolation, so that the calculated values of attenuation of rays at the sites of defective channels are close to the actual values, thereby significantly improving the quality of image reconstruction and ensuring the quality of clinical diagnosis. With supplement to texture of areas to be recovered, accurate calculation of attenuation of rays can be ensured even if there are continuous defective channels.

BRIEF DESCRIPTION OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE INVENTION

Figure 1:
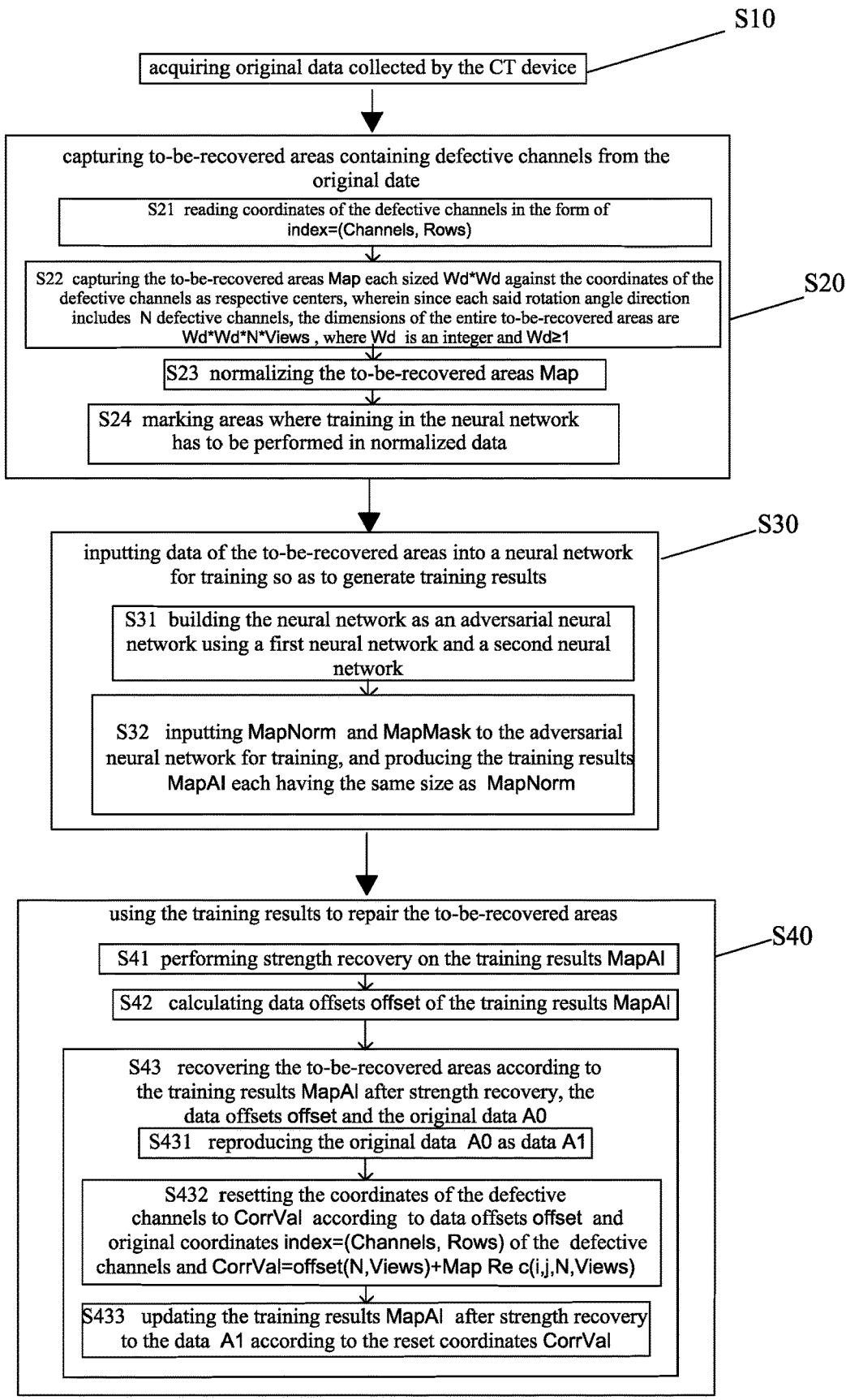
FIG. 1 is a flowchart of a method for calibrating defective channels of a CT device according to the present invention.
Figure 2:
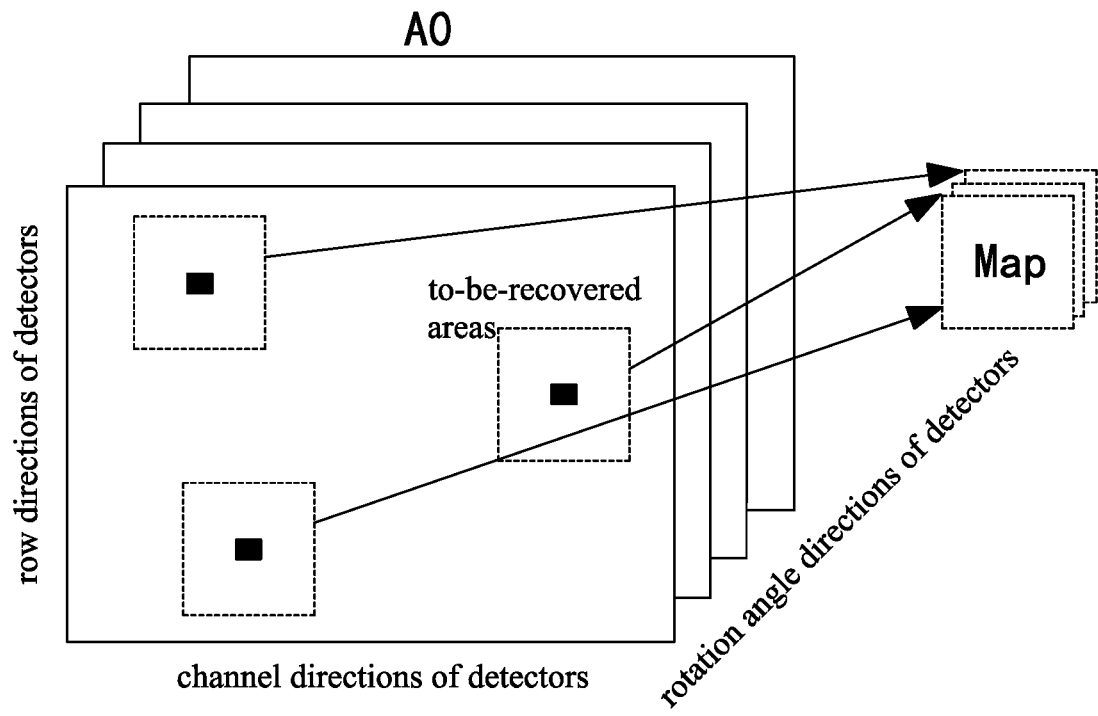
FIG. 2 shows capture of to-be-recovered areas Map according to the present invention.
Figure 3:
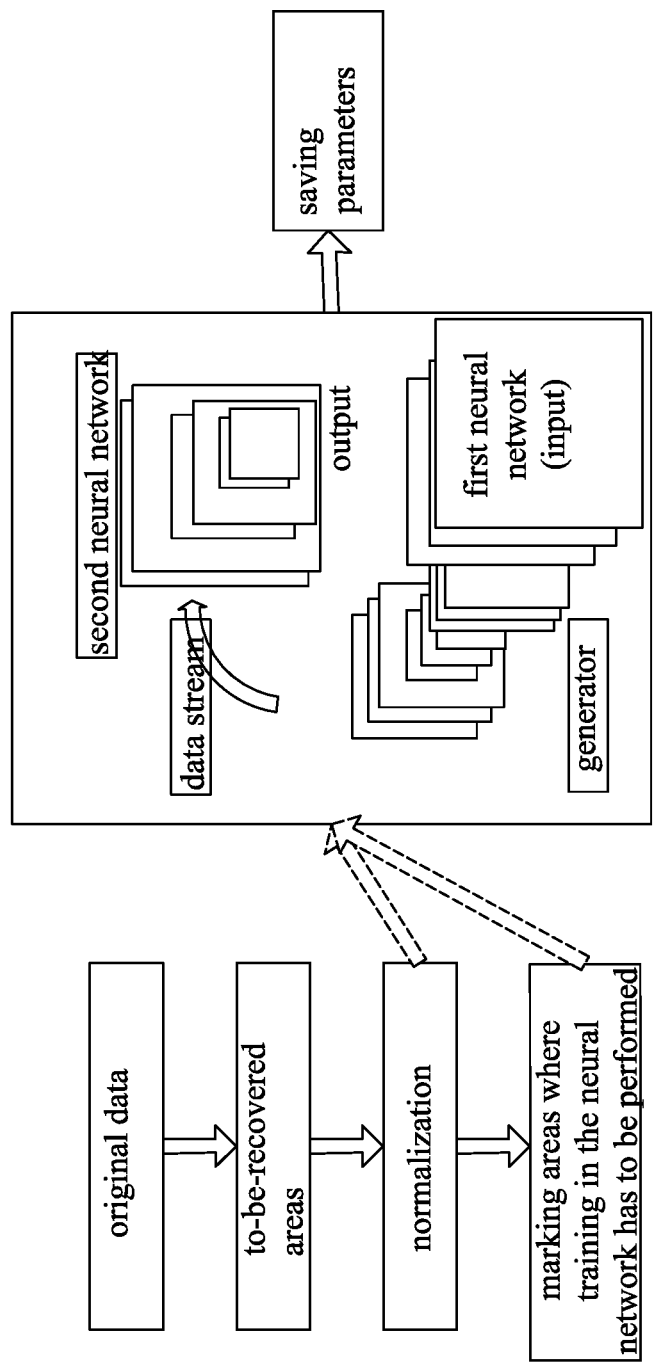
FIG. 3 illustrates neural network training according to the present invention.
Figure 4:
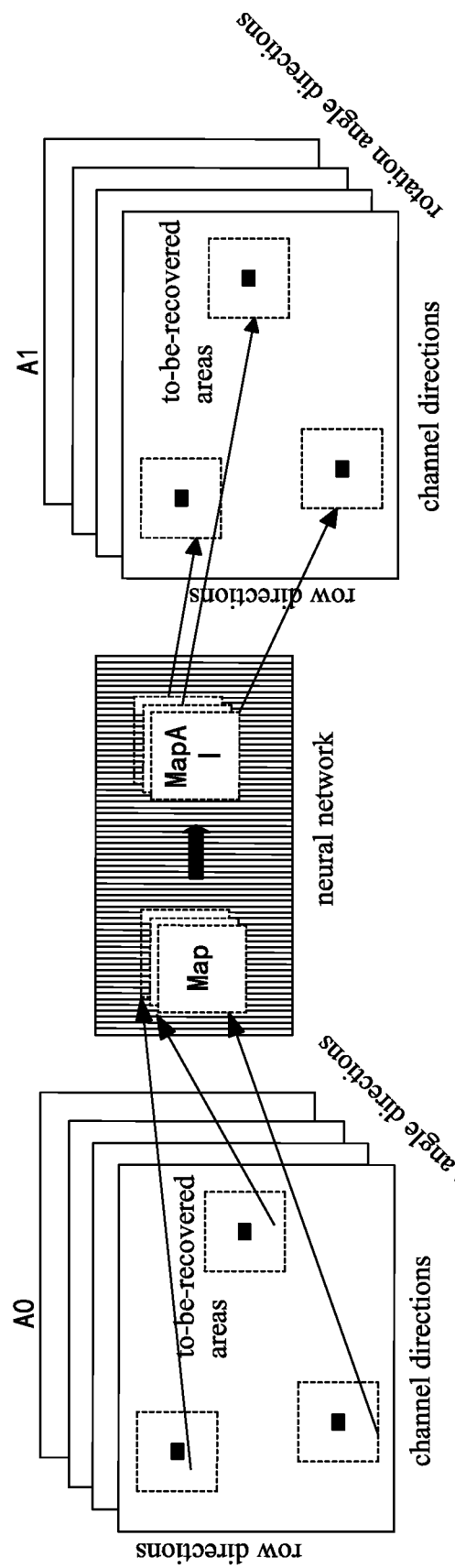
FIG. 4 illustrates a method for calibrating defective channels of a CT device according to the present invention.
Figure 5:
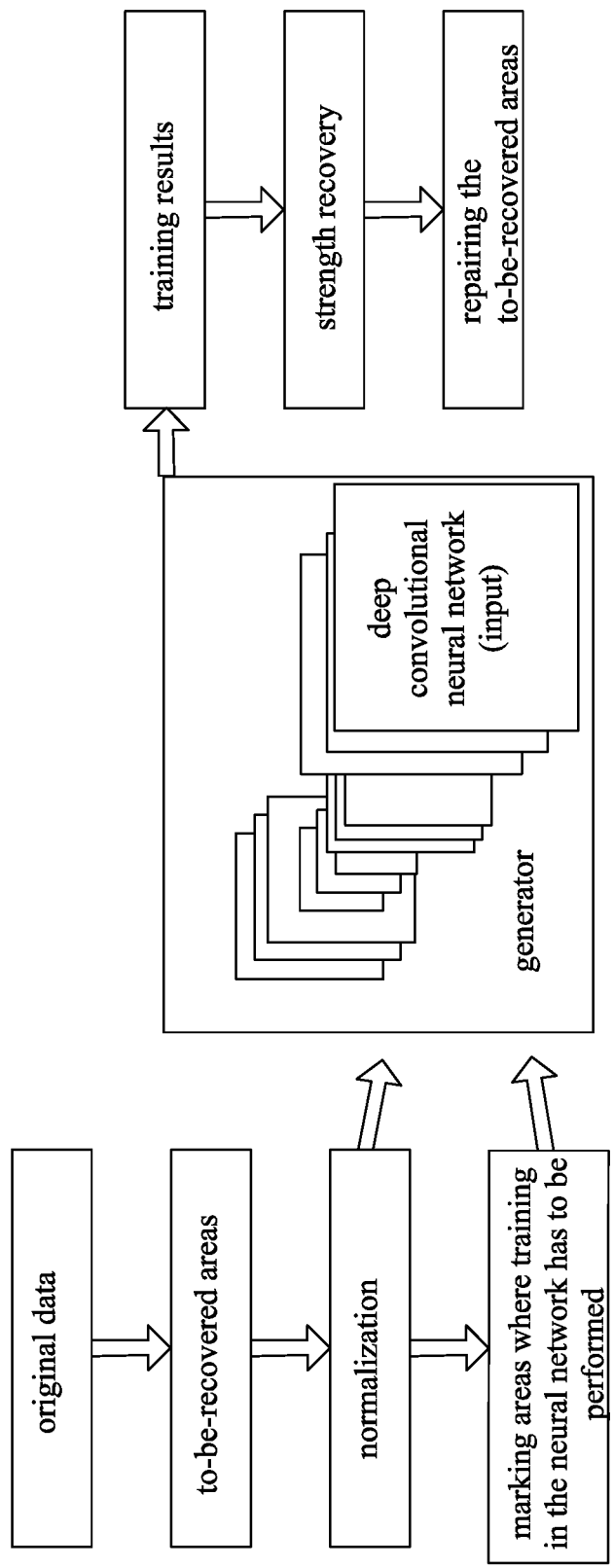
FIG. 5 is an applied diagram of a neural network of the present invention.

Referring to FIG. 1 through FIG. 5, a preferred embodiment of a method for calibrating defective channels of a CT device according to the present invention comprises the following steps:

in the step S10, acquiring original data collected by the CT device;

in the step S20, capturing to-be-recovered areas from the original data, wherein the to-be-recovered areas contain the defective channels of the CT device, in which the to-be-recovered area may be a single defective channel, or a defective channel cluster composed of multiple defective channels;

in the step S30, inputting data of the to-be-recovered areas into a neural network for training so as to produce training results; and in the step S40, using the training results to repair the to-be-recovered areas.

The step S10 particularly is:

acquiring the original data collected by the CT device as three-dimensional data A0(Channels, Rows, Views), where Channels represents channel directions of detectors of the CT device, Rows represents row directions of the detectors, Views represents rotation angle directions of the detectors, each said rotation angle direction covering N defective channels, N≥1; the original data being the sine data of A0 after calibration.

in the step S20 particularly involves:

in the step S21, reading coordinates of the defective channels in the form of index=(Channel s, Views), namely taking the channel directions of the detectors of the CT device as the abscissa and taking the row directions of the detectors as the ordinate;

in the step S22, capturing the to-be-recovered areas Map each sized Wd*Wd against the coordinates of the defective channels as respective centers, wherein since each said rotation angle direction includes N defective channels, the dimensions of the entire to-be-recovered areas are Wd*Wd*N*Views, where Wd is an integer and Wd≥1;

in the step S23, normalizing the to-be-recovered areas Map, wherein normalization is used to simplify calculation, through which a dimensional expression is converted to a dimensionless expression, becoming a scalar; and in the step S24, marking areas where training in the neural network has to be performed in normalized data.

The step S23 particularly is:

defining an operator Norm(N, Views)=maximum (Map (:, :, N, Views)), which represents finding the maximum of each said to-be-recovered area Map sized Wd*Wd; and normalizing the to-be-recovered areas Map to [0, 1]: MapNorm=Map/Norm, or normalizing the to-be-recovered areas Map to [−1, 1]: MapNorm=Map/Norm*2−1, where MapNorm represents the normalized data.

The step S24 particularly is:

marking the areas needing training in the neural network as MapMask, and $$MapMask = \begin{cases} C & \left| i - \frac{W_d}{2}, j - \frac{W_d}{2} \right| < h \\ MapNorm & else \end{cases};$$

where C represents an arbitrarily marked mask value; h represents the width of mask; the operator ∥ represents calculating the 2nd norm; i represents a number of the channel directions of the detectors, and i>0; j represents a number of the row directions of the detectors, and j>0. The 2nd norm refers to a 2-norm of the matrix A, being the value of the square root of the maximum characteristic root of the product of the conjugate transpose matrix of A and the matrix A, and being a linear distance between two vector matrices in a space. This is similar to finding a linear distance between two points in a checkerboard.

The step S30 particularly involves:

in the step S31, building the neural network as an adversarial neural network using a first neural network and a second neural network, wherein the first neural network is preferably a U-Net and the second neural network is preferably a deep convolutional neural network; and in the step S32, inputting MapNorm and MapMask to the adversarial neural network for training, and producing the training results MapAI each having the same size as MapNorm.

The adversarial neural network is a network where the first neural network and the second neural network game with each other.

For example, G is a network that produces an image based on a random noise z it receives, with the noise written as G(z); and D is a discriminator network that determines whether an image is "real" or not based on an input parameter, x. Therein, x represents an image and output D(x) represents the probability that x is a real image, in which where the value is 1, it indicates that the image is 100% a real image, and where the output is 0, it indicates that the image is absolutely not a real image. During training, the generative network G is designed to generate real images to cheat the discriminator network D, and D is designed to discriminate the images generated by G from the real image. In this way, G and D form a dynamic "gaming process". The ideal result of this process is that G produces the image G(z) as real as possible to fail the discrimination so that it is difficult for D to determine whether the image produced by G is real or not. Thus, a generative model G generating images can be obtained.

The step S40 particularly involves:

in the step S41, performing strength recovery on the training results MapAI;

in the step S42, calculating data offsets offset of the training results MapAI, which is for correction of the training results of the neural network, and where the actual data offset off set of the training results is little or offset=0, correction made to the training result based on the data offsets offset can be omitted; and in the step S43, recovering the to-be-recovered areas according to the training results MapAI after strength recovery, the data offsets offset and the original data A0.

The step S41 particularly is:

defining the data of each said rotation angle direction after strength recovery MapRec (:, :, N, Views)=(MapAI, N, Views)+1)*Norm(N, Views)/2.

The step S42 particularly involves:

defining a matrix template sized Wd*Wd, $$Ref\ Mask = \begin{cases} 1 & L1 < \left| i - \frac{W_d}{2}, j - \frac{W_d}{2} \right| < L2 \\ 0 & else \end{cases},$$

and L2−L1>h; and defining the data offsets offset=(A0−MapRec)*Ref Mask/sum(Ref Mask), where sum(Ref Mask) represents the sum of all elements in Ref/Mask The step S43 particularly involves:

the step S431, reproducing the original data A0 as data A1;

the step S432, resetting the coordinates of the defective channels to Corr Val according to the data offsets offset and the original coordinates index=(Channels, Rows) of the defective channels, and Corr Val=offset(N, Views)+Map Rec (i, j, N, Views); and the step S433, updating the training results MapAI after strength recovery to the data A1 according to the reset coordinates Corr Val.

To sum up, the present invention advantageously employs a neural network to perform training on data in areas to be recovered and thereby supplementing texture of the to-be-recovered areas but not simply performing interpolation, so that the calculated values of attenuation of rays at the sites of defective channels are close to the actual values, thereby significantly improving the quality of image reconstruction and ensuring the quality of clinical diagnosis. With supplement to texture of areas to be recovered, accurate calculation of attenuation of rays can be ensured even if there are continuous defective channels.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A method for calibrating defective channels of a CT (computed tomography) device, comprising:
    a step S10, acquiring original data collected by the CT device;
    a step S20, capturing to-be-recovered areas from the original data, wherein the to-be-recovered areas contain the defective channels of the CT device;
    a step S30, inputting data of the to-be-recovered areas to a neural network for training so as to generate training results; and
    a step S40, using the training results to repair the to-be-recovered areas;
    wherein the step S10 particularly comprises:
    acquiring the original data collected by the CT device as three-dimensional data A0(Channels, Rows, Views), where Channels represents channel directions of detectors of the CT device, Rows represents row directions of the detectors, Views represents rotation angle directions of the detectors, each said rotation angle direction covering N defective channels;
    wherein the step S20 particularly comprises:
    a step S21, reading coordinates of the defective channels in the form of index=(Channels, Rows);
    a step S22, capturing the to-be-recovered areas Map each sized Wd*Wd against the coordinates of the defective channels as respective centers, with dimensions of the entire to-be-recovered areas being Wd*Wd*N*Views, where Wd is an integer and Wd≤1;
    a step S23, normalizing the to-be-recovered areas Map; and
    a step S24, marking areas where training in the neural network has to be performed in normalized data.

2. The method of claim 1, wherein the step S23 particularly comprises:
    defining an operator Norm(N, Views)=maximum(Map (:,:, N,Views)), which represents finding a maximum of each said to-be-recovered area Map sized Wd*Wd; and
    normalizing the to-be-recovered areas Map to [0,1]: MapNorm=Map/Norm or normalizing the to-be-recovered areas to [−1,1]: MapNorm=Map/Norm*2−1, where MapNorm represents the normalized data.

3. The method of claim 2, wherein the step S24 particularly comprises:

marking the areas needing training in the neural network as MapMask , and $$MapMask = \begin{cases} C & \left|i - \frac{W_d}{2}, j - \frac{W_d}{2}\right| < h \\ MapNorm & else \end{cases};$$

where c represents an arbitrarily marked mask value; h represents a width of mask; the operator ‖ represents calculation of a 2nd norm; i represents a number of the channel directions of the detectors, and i>0; and j represents a number of the row directions of the detectors, and j>0.

4. The method of claim 3, wherein the step S30 particularly comprises:
   a step S31, building the neural network as an adversarial neural network using a first neural network and a second neural network; and
   a step S32, inputting MapNorm and MapMask to the adversarial neural network for training, and producing the training results MapAI each having the same size as MapNorm.

5. The method of claim 4, wherein the step S40 particularly comprises:
   a step S41, performing strength recovery on the training results MapAI;
   a step S42, calculating data offsets offset of the training results MapAI; and
   a step S43, recovering the to-be-recovered areas according to the training results MapAI after strength recovery, the data offsets offset and the original data A0.

6. The method of claim 5, wherein the step S41 particularly is:
   defining data of each said rotation angle direction after strength recovery, MapRec (:,:,N,Views)=(MapAI(:,:,N,Views)+1)*Norm(N,Views)/ 2 .

7. The method of claim 6, wherein the step S42 particularly comprises:
   defining a matrix template sized wd*wd , $$Ref\ Mask = \begin{cases} 1 & L1 < \left|i - \frac{W_d}{2}, j - \frac{W_d}{2}\right| < L2 \\ 0 & else \end{cases},$$

and L2−L1>h ; and
   defining the data offsets offset=(A0−MapRec)*RefMask/sum(RefMask), where sum(RefMask) represents a sum of all elements in RefMask.

8. The method of claim 7, wherein the step S43 particularly comprises:
   a step S431, reproducing the original data A0 as data A1;
   a step S432, resetting the coordinates of the defective channels to CorrVal according to the data offsets offset and the original coordinates index=(Channels,Rows) of the defective channels, and CorrVal=offset(N,Views)+MapRec(i,j,N,Views); and
   a step S433, updating the training results MapAI after strength recovery to the data A1 according to the reset coordinates CorrVal.

* * * * *